United States Patent [19]
Lin

[11] Patent Number: 5,571,162
[45] Date of Patent: Nov. 5, 1996

[54] TRANSVENOUS DEFIBRILLATION LEAD WITH SIDE HOOKS

[75] Inventor: Jack H. Lin, Lake Jackson, Tex.

[73] Assignee: Intermedics, Inc., Angleton, Tex.

[21] Appl. No.: 475,011

[22] Filed: Jun. 7, 1995

[51] Int. Cl.⁶ ..................................................... A61N 1/05
[52] U.S. Cl. .......................... 607/122; 607/126; 607/127; 607/128
[58] Field of Search .................................. 607/122, 126, 607/127, 128

[56] References Cited

U.S. PATENT DOCUMENTS

| | | | |
|---|---|---|---|
| 3,814,104 | 6/1974 | Imich et al. | 607/128 |
| 3,902,501 | 9/1975 | Citron et al. | 128/418 |
| 3,939,843 | 2/1976 | Smyth | 607/126 |
| 3,943,936 | 3/1976 | Rasor et al. | 128/419 |
| 4,233,992 | 11/1980 | Bisping | 128/785 |
| 4,280,512 | 7/1981 | Karr et al. | 607/128 |
| 4,378,023 | 3/1983 | Trabucco | 128/785 |
| 4,721,118 | 1/1988 | Harris | 128/785 |
| 4,858,623 | 8/1989 | Bradshaw et al. | 607/116 |
| 5,179,962 | 1/1993 | Dutcher et al. | 128/785 |
| 5,257,634 | 11/1993 | Kroll | 607/128 |
| 5,314,462 | 5/1994 | Heil, Jr. et al. | 607/128 |
| 5,476,500 | 12/1995 | Fain et al. | 607/126 |

FOREIGN PATENT DOCUMENTS

| | | | |
|---|---|---|---|
| 4967A | 10/1979 | European Pat. Off. | 607/128 |
| 529578A | 2/1987 | Germany | 607/128 |

*Primary Examiner*—William E. Kamm
*Assistant Examiner*—Carl H. Layno
*Attorney, Agent, or Firm*—Richard L. Robinson

[57] ABSTRACT

A transvenous implantable defibrillation lead includes a conductor and inner and outer coaxial cylindrical electrodes. The inner electrode is connected to the conductor, and the outer electrode is connected to a sheath overlying the conductor in rotatable relationship thereto. The sheath is fixed to the outer cylindrical electrode so that rotation of the sheath relative to the conductor results in rotation of the inner and outer cylindrical electrodes relative to each other. The inner electrode has a plurality of hooks extending generally transversely and tangentially thereto, with the hooks being biased such that the terminal ends of the hooks tend to spring outwardly from the inner electrode. The hooks are constrained against the inner cylindrical electrode by the outer cylindrical electrode, except that a window in the outer electrode permits the hooks to spring outwardly therethrough upon rotation of the outer electrode relative to the inner electrode. Once the hooks are so exposed, rotation of the inner and outer electrodes in unison permits the hooks to engage cardiac tissue. The hooks provide fixation as well as conducting electrical stimulus to the cardiac tissue.

6 Claims, 1 Drawing Sheet

5,571,162

TRANSVENOUS DEFIBRILLATION LEAD WITH SIDE HOOKS

BACKGROUND OF THE INVENTION

1. Field of the Invention

The present invention relates generally to leads for use with cardiac stimulators, and more particularly to transvenous defibrillation leads and fixation mechanisms therefor.

2. Background Art

Various mechanisms have been proposed and used for fixing the distal end of a transvenous lead in place within a chamber of the heart, including tines, hooks, and helical screws. In some cases, the fixation member provides mechanical fixation only, whereas in other cases the fixation member also serves as a conductor to deliver electrical stimulus to cardiac tissue. Among endocardial leads and electrodes intended for use as shock electrodes in combination with implantable defibrillators, the more common approach has been to use electrodes having a relatively great length and surface area, and to secure the lead in contact with cardiac tissue only at the distal end thereof. In general, the shock electrode itself has not been secured in contact with cardiac tissue, which is believed to lower the defibrillation threshold and permit use of an electrode having a smaller surface area.

SUMMARY OF THE INVENTION

In accordance with one aspect of the present invention, there is provided a transvenous defibrillation lead including a conductor, and an inner cylindrical electrode mechanically and electrically connected to the conductor at a distal end thereof. The inner cylindrical electrode has a plurality of hooks mechanically and electrically connected thereto and extending generally transversely to a longitudinal axis of the lead and extending generally tangentially from the inner cylindrical electrode. The hooks are biased to spring outwardly from the inner cylindrical electrode when unconstrained. An outer hollow cylindrical electrode is disposed coaxially about the inner cylindrical electrode and generally overlies and constrains the hooks. The outer cylindrical electrode has a window therethrough of sufficient size and orientation to permit the hooks to spring outwardly away from the inner cylindrical electrode and through the window so as to overlie the outer cylindrical electrode in spaced relationship upon relative rotation of the outer cylindrical electrode relative to the inner cylindrical electrode. A sheath overlies the conductor and is rotatable relative thereto. The sheath is connected to the outer cylindrical electrode such that rotation of the sheath relative to the conductor results in rotation of the outer cylindrical electrode relative to the inner cylindrical electrode.

It is an object of the present invention to provide an improved transvenous defibrillation lead.

Other objects and advantages of the present invention will be apparent from the following descriptions of a preferred embodiment made with reference to the drawings.

DETAILED DESCRIPTION OF THE PREFERRED EMBODIMENT

Figure 1:
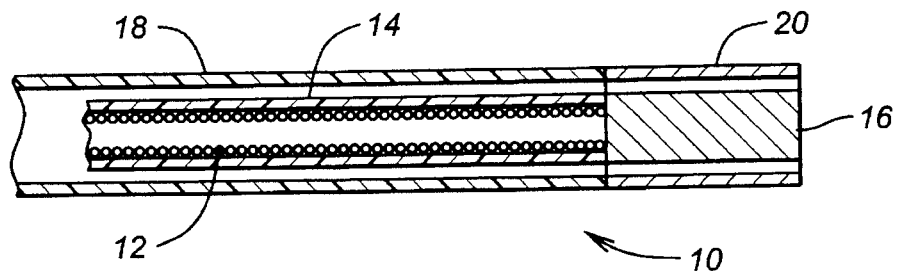
FIG. 1 is a longitudinal-sectional view of a lead arranged in accordance with the present invention.

Referring to FIG. 1, there is illustrated a transvenous defibrillation lead 10 in accordance with the present invention. Lead 10 includes a helical wire coil conductor 12 extending the length thereof, insulated by an overlying layer 14 of polyurethane, or silicone rubber, or other suitable biocompatible material. Coil conductor 12 is mechanically and electrically connected to a cylindrical inner electrode 16 at the distal end of lead 10. Surrounding coil conductor 12 and insulating layer 14 is a sheath 18 that is insulative in nature, and that is sufficiently stiff and loose fitting relative to insulating layer 14 that it can be rotated relative to conductor 12 and insulating layer 14 to transmit torque to a hollow cylindrical outer electrode 20 that is disposed coaxially about cylindrical inner electrode 16. Sheath 18 is preferably bonded to outer electrode 20 in such a manner that rotation of sheath 18 about the longitudinal axis of lead 10 results in a corresponding rotation of outer electrode 20 relative to inner electrode 16.

Figure 2:
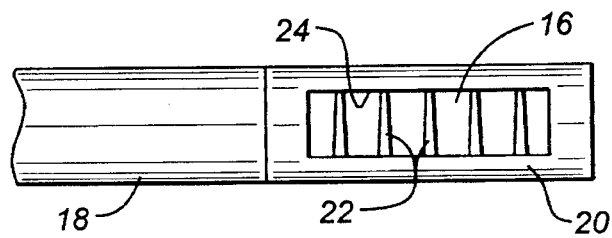
FIG. 2 is an elevational view of the lead of FIG. 1, particularly showing a detail of the electrode portion and fixation hooks.
Figure 3:
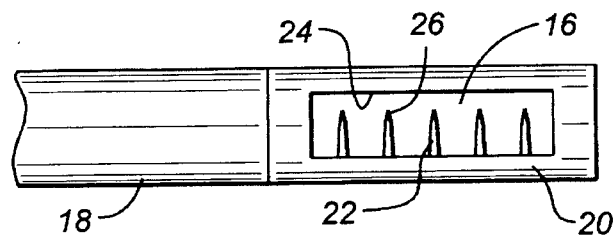
FIG. 3 is another elevational view of the lead of FIG. 1, similar to FIG. 2, in which the two parts of the electrode have been rotated relative to each other to expose the terminal ends of the fixation hooks.
Figure 4:
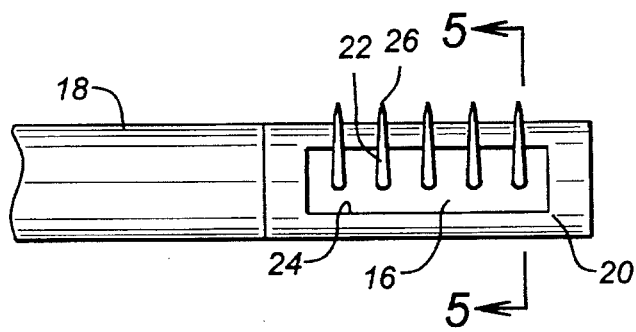
FIG. 4 is another elevational view of the lead of FIG. 1, similar to FIGS. 2 and 3, in which the two parts of the electrode have been rotated farther relative to each other to permit the fixation hooks to extend.

Referring to FIGS. 2, 3 and 4, inner and outer electrodes 16 and 20 are illustrated in somewhat more detail, and the effect of relative rotation of electrodes 16 and 20 is shown. It should be understood that inner electrode 16 has bonded to its outer surface a plurality of electrically conductive hooks 22, each of which lies substantially parallel to the others in a direction generally transverse to the longitudinal axis of lead 10. Hooks 22 are bonded to the surface of inner electrode 16 along a longitudinal line, and emerge from the cylindrical surface of inner electrode 16 generally tangentially thereto. Hooks 22 can be regarded as lying in a common curved "plane" that curves concavely about the longitudinal axis of lead 10. The radius of curvature of the curved "plane," when the hooks 22 are in an unconstrained state, is greater than the radius of curvature of inner electrode 16 and therefore hooks 22 naturally tend to spring elastically away from the surface of inner electrode 16 when unconstrained. Outer electrode 20 generally overlies hooks 22 and constrains them to lie closely adjacent the outer surface of inner electrode 16. However, outer electrode 20 includes an axially elongated rectangular window 24 through the wall thereof, which window 24 extends axially beyond hooks 22 at each end and is of sufficient width to allow the terminal ends 26 of hooks 22 to spring radially outwardly beyond the outer surface of outer electrode 20 under certain conditions.

In FIG. 2, outer electrode 20 is shown disposed such that the terminal ends 26 of hooks 22 are constrained between outer electrode 20 and inner electrode 16.

In FIG. 3, outer electrode 20 has been rotated relative to inner electrode 16 via relative rotation of sheath 18 and conductor/insulator 12, 14, until terminal ends 26 of hooks 22 are released and spring outwardly beyond the outer surface of outer electrode 20.

Figure 5:
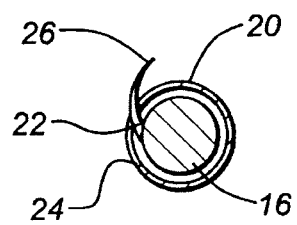
FIG. 5 is a cross-sectional view of the lead of FIG. 1, taken along section plane 5—5 of FIG. 4, and viewed in the direction of the arrows.

In FIGS. 4 and 5, outer electrode 20 has been rotated further relative to inner electrode 16 so as to fully expose hooks 22 such that terminal ends 26 of hooks 22 are no longer disposed within the confines of window 24 but extend outwardly through window 24 and overlie the outer surface of outer electrode 20, albeit spaced therefrom.

In use, the lead 10 of the present invention is introduced transvenously in conventional fashion into the ventricle of the heart with the hooks 22 fully sheathed by outer electrode 20 to prevent injury to the patient as the lead is passed through blood vessels, heart chambers and valves. Once positioned properly in the ventricle, relative rotation between electrodes 16 and 20 is effected as described above to expose hooks 22, and inner electrode 16 and outer electrode 20 are then rotated in unison to engage the terminal ends 26 of hooks 22 into cardiac tissue, preferably the septum. Such action fixes the electrode in place and, because the hooks 22 are electrically connected to electrode 16 and spaced apart equally to create more edge effects and to distribute the electrical energy uniformly through the septum, it is believed to result in a lower defibrillation threshold than would otherwise be obtained.

What is claimed is:

1. A transvenous defibrillation lead, comprising:

a conductor;

an electrode mechanically and electrically connected to said conductor at a distal end thereof, said electrode having a plurality of hooks extending generally transversely to a longitudinal axis of said lead, each of said plurality of hooks having a first end mechanically and electrically connected to said electrode and having a second end free;

means connecting said electrode to said plurality of hooks for biasing each of said second ends to spring outwardly from said electrode when unconstrained;

means for alternately constraining and unconstraining said hooks, including a hollow cylinder disposed coaxially about said electrode and having a window therethrough, said hollow cylinder having a first orientation in which said hooks are overlain and constrained by said cylinder, and a second orientation in which said hooks are unconstrained and extend outwardly through said window so as to overlie said hollow cylinder in spaced relationship, said hollow cylinder being movable between said first and second orientations upon rotation of said outer hollow cylinder relative to said electrode; and a sheath overlying said conductor and rotatable relative thereto, said sheath being connected to said hollow cylinder such that rotation of said sheath relative to said conductor results in rotation of said hollow cylinder relative to said electrode.

2. The lead of claim 1, in which said hooks extend from said electrode along an axial line.

3. The lead of claim 1, in which said hooks lie generally parallel to each other in a curved plane.

4. The lead of claim 3, in which said electrode is cylindrical and said curved plane curves concavely about the longitudinal axis of said lead and has a radius of curvature that is greater than that of said cylindrical electrode when said hooks are unconstrained.

5. The lead of claim 3, in which said electrode further comprises equally spaced intervals separating said hooks.

6. The lead of claim 1, and further including an insulator layer overlying said conductor.

* * * * *